United States Patent
Culver et al.

(10) Patent No.: US 8,383,237 B2
(45) Date of Patent: Feb. 26, 2013

(54) PREPARATION OF SILICA STABILIZED BIOLOGICAL TEMPLATES FOR THE PRODUCTION OF METAL AND LAYERED NANOPARTICLES

(75) Inventors: James N. Culver, Potomac, MD (US); Elizabeth Royston, Walkersville, MD (US); Adam Brown, Berwyn Heights, MD (US); Michael Harris, Lafeyette, IN (US)

(73) Assignees: University of Maryland, College Park, Baltimore, MD (US); Purdue Research Foundation, West Lafayette, IN (US)

( * ) Notice: Subject to any disclaimer, the term of this patent is extended or adjusted under 35 U.S.C. 154(b) by 228 days.

(21) Appl. No.: 12/790,926

(22) Filed: May 31, 2010

(65) Prior Publication Data

US 2011/0014472 A1    Jan. 20, 2011

Related U.S. Application Data

(60) Provisional application No. 61/182,798, filed on Jun. 1, 2009.

(51) Int. Cl.
*B32B 5/16* (2006.01)
*B05D 7/00* (2006.01)

(52) U.S. Cl. ......... 428/403; 427/214
(58) Field of Classification Search .......... None
See application file for complete search history.

(56) References Cited

U.S. PATENT DOCUMENTS

| | | |
|---|---|---|
| 2004/0028694 A1 | 2/2004 | Young et al. |
| 2004/0197884 A1 | 10/2004 | Okuda et al. |
| 2008/0170982 A1 * | 7/2008 | Zhang et al. ............... 423/447.3 |
| 2009/0029441 A1 * | 1/2009 | Wang et al. ................ 435/235.1 |
| 2009/0155617 A1 * | 6/2009 | Kim et al. .................... 428/611 |
| 2010/0093562 A1 | 4/2010 | Culver et al. |
| 2011/0014472 A1 * | 1/2011 | Culver et al. ................. 428/403 |

FOREIGN PATENT DOCUMENTS

WO    WO2004/065928    8/2004

OTHER PUBLICATIONS

Tai et al. (Sensors and Actuators B. 2007; 125: 644-650).*
sequence alignment of SEQ ID No. 1 with UniProt database accession No. A7M754, submitted Oct. 2, 2007 by Choi et al.*
C.B. Mao, C.E. Flynn, A. Hayhurst, R. Sweeney, J.F. Qi, G. Georgiou, B. Iverson and A.M. Belcher, *Proc. Natl. Acad. Sci. USA* 100 (2003), p. 6946.
K.T. Nam, D.W. Kim, P.J. Yoo, C.Y. Chiang, N. Meethong, P.T. Hammond, Y.M. Chiang and A.M. Belcher, *Science* 312 (2006), p. 885.
W. Shenton, T. Douglas, M. Young, G. Stubbs and S. Mann, *Adv. Mater.* 11 (1999), p. 253.
V.V. Hardikar and E. Matijevic, *J. Colloid Interface Sci.* 221 (2000), p. 133.
E. Dujardin, C. Peet, G. Stubbs, J.N. Culver and S. Mann, *Nano Lett.* 3 (2003), p. 413.
C.E. Fowler, W. Shenton, G. Stubbs and S. Mann, *Adv. Mater.* 13 (2001), p. 1266.
C. Radloff, R.A. Vaia, J. Brunton, G.T. Bouwer and V.K. Ward, *Nano Lett.* 5 (2005), p. 1187.

(Continued)

*Primary Examiner* — Shanon A Foley
(74) *Attorney, Agent, or Firm* — Marianne Fuierer; Moore & Van Allen, PLLC

(57) ABSTRACT

The present invention relates to a system and method providing for increased silica growth on a bio-template, wherein the bio-template is pretreated with aniline to produce a uniform silica attractive surface and yielding a significant silica layers of at least 10 nm, and more preferably at least 20 nm in thickness, thereby providing for a high degree of stability to the bio-template.

16 Claims, 12 Drawing Sheets

OTHER PUBLICATIONS

J.M. Hooker, E.W. Kovacs and M.B. Francis, *J. Am. Chem. Soc.* 126 (2004), p. 3718.
C.E. Flynn, S.W. Lee, B.R. Peelle and A.M. Belcher, *Acta Mater.* 51 (2003), p. 5867.
S.W. Lee, C.B. Mao, C.E. Flynn and A.M. Belcher, *Science* 296 (2002), p. 892.
C.B. Mao, D.J. Solis, B.D. Reiss, S.T. Kottmann, R.Y. Sweeney, A. Hayhurst, G. Georgiou, B. Iverson and A.M. Belcher, *Science* 303 (2004), p. 213.
S.Y. Lee, J.W. Choi, E. Royston, D.B. Janes, J.N. Culver and M.T. Harris, *J. Nanosci. Nanotechnol.* 6 (2006), p. 974.
S.Y. Lee, J.N. Culver and M.T. Harris, *J. Colloid Interface Sci.* 297 (2006), p. 554.
E. Royston, S.Y. Lee, J.N. Culver and M.T. Harris, *J. Colloid Interface Sci.* 298 (2006), p. 706.
T.L. Schlick, Z.B. Ding, E.W. Kovacs and M.B. Francis, *J. Am. Chem. Soc.* 127 (2005), p. 3718.
S.Y. Lee, E. Royston, J.N. Culver and M.T. Harris, *Nanotechnology* 16 (2005), p. S435.
H.M. Yi, S. Nisar, S.Y. Lee, M.A. Powers, W.E. Bentley, G.F. Payne, R. Ghodssi, G.W. Rubloff, M.T. Harris and J.N. Culver, *Nano Lett.* 5 (2005), p. 1931.
M. Knez, M. Sumser, A.M. Bittner, C. Wege, H. Jeske, T.P. Martin and K. Kern, *Adv. Funct. Mater.* 14 (2004), p. 116.
W.L. Liu, K. Alim, A.A. Balandin, D.M. Mathews and J.A. Dodds, *Appl. Phys. Lett.* 86 (2005).
G. Stubbs, *Semin. Virol.* 1(1990), p. 405.
K. Namba, R. Pattanayek and G. Stubbs, *J. Mol. Biol.* 208 (1989), p. 307.
K. Keren, R.S. Berman, E. Buchstab, U. Sivan and E. Braun, *Science* 302 (2003), p. 1380.
R.J. Tseng, C.L. Tsai, L.P. Ma and J.Y. Ouyang, *Nat. Nanotechnol.* 1 (2006), p. 72.
Kobayashi, V. Salgueirino-Maceira and L.M. Liz-Marzan, *Chem. Mater.* 13 (2001), p. 1630.
W. Stober, A. Fink and E. Bohn, *J. Colloid Interface Sci.* 26 (1968), p. 62.
J.H. Kim, J.S. Kim, H. Choi, S.M. Lee, B.H. Jun, K.N. Yu, E. Kuk, Y.K. Kim, D.H. Jeong, M.H. Cho and Y.S. Lee, *Anal. Chem.* 78 (2006), p. 6967.
Y.L. Shi and T. Asefa, *Langmuir* 23 (2007), p. 9455.
T. Pham, J.B. Jackson, N.J. Halas and T.R. Lee, *Langmuir* 18 (2002), p. 4915.
M. Schierhorn and L.M. Liz-Marzan, *Nano Lett.* 2 (2002), p. 13.
S. Ahrland, I. Grenthe and B. Noren, *Acta Chem. Scand.* 14 (1960), p. 1059.
Y.T. Lim, O.O. Park and H.T. Jung, *J. Colloid Interface Sci.* 263 (2003), p. 449.
Z. Niu, J. Liu, L.A. Lee, M.A. Bruckman, D. Zhao, G. Koley and Q. Wang, *Nano Lett.* 7 (2007), p. 3729.
M. Adachi, T. Harada and M. Harada, *Langmuir* 15 (1999), p. 7097.
M. Adachi, T. Harada and M. Harada, *Langmuir* 16 (2000), p. 2376.
I. Ichinose and T. Kunitake, *Adv. Mater.* 14 (2002), p. 344.
M. Endo, H.X. Wang, M. Fujitsuka and T. Majima, *Chem. Eur. J.* 12 (2006), p. 3735.
S.L. Westcott, S.J. Oldenburg, T.R. Lee and N.J. Halas, *Langmuir* 14 (1998), p. 5396.
E. Royston, A. Ghosh, P. Kofinas, M.T. Harris and J.N. Culver, *Langmuir* 24 (2008), p. 906.
C.J. Brinker and G.W. Scherer, Sol-Gel Science: The Physics and Chemistry of Sol-Gel Processing, Academic Press, Boston (1990).
R.K. Iler, The Chemistry of Silica: Solubility, Polymerization, Colloid and Surface Properties, and Biochemistry, John Wiley & Sons, New York (1979).
D. Christendat, T. Abraham, Z. Xu and J. Masliyah, *J. Adhes. Sci. Technol.* 19 (2005), p. 149.
W. Rasband, ImageJ, 1.33u, National Institutes of Health, USA, 2004.
I.P. Suzdalev, V.I. Goldanskii, E.F. Makarov, A.S. Planchinda and L.A. Korytko, *Sov. Phys. JETP* 22 (1966), p. 979.
Y. Kobayashi, V. Salgueirino-Maceira and L.M. Liz-Marzan, *Chem. Mater.* 13 (2001), p. 1630.
Y. Kobayashi, Y. Tadaki, D. Nagao and M. Konno, *J. Colloid Interface Sci.* 283 (2005), p. 601.

\* cited by examiner

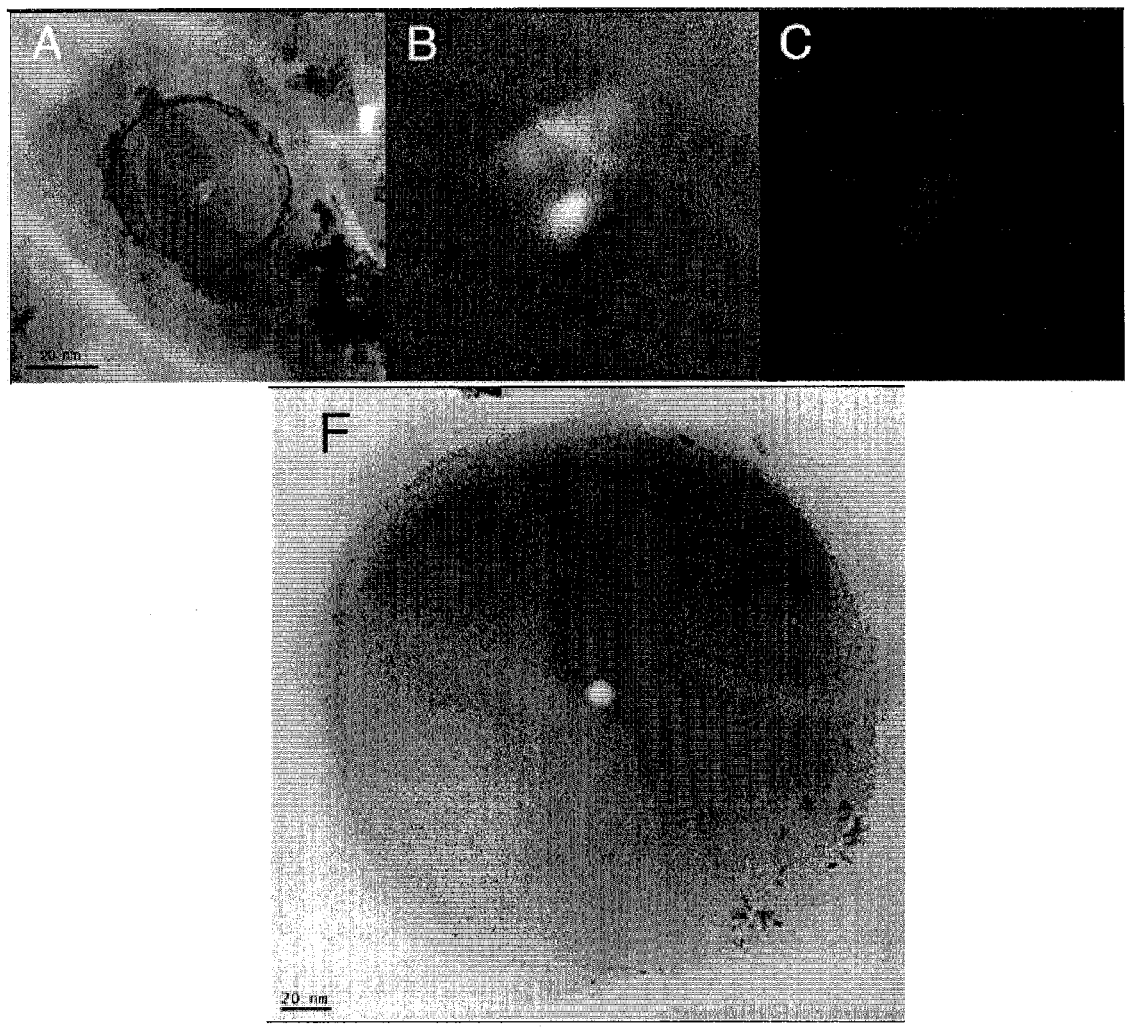
Figure 8 A, B, C and F

PREPARATION OF SILICA STABILIZED BIOLOGICAL TEMPLATES FOR THE PRODUCTION OF METAL AND LAYERED NANOPARTICLES

CROSS-REFERENCE TO RELATED APPLICATION

The present application claims priority to U.S. Provisional Patent Application No. 61/182,799 filed on Jun. 1, 2009, the contents of which are hereby incorporated by reference herein for all purposes.

STATEMENT OF GOVERNMENT RIGHTS

This work was supported by a grant from the Department of Energy under contract number DEFG02-02ER45975-03527021 and the United States Government has rights to this invention.

BACKGROUND OF THE INVENTION

1. Field of the Invention

The present invention relates to stable metal nanoparticles and more particularly to a bio-template, such as tobacco mosaic virus (TMV), coated with aniline which provides for a stable platform for deposition of a metal oxide layer having a thickness greater than 20 nm thereby providing for a robust platform for the deposition of metals.

2. Background of the Related Art

The exploitation of biologically derived material for the assembly of micro- and nanoscale devices is a rapidly expanding field. At present the adaptation of biological molecules into nanodevices has generally been used to impart novel functionalities, such as nucleic acid recognition or antigen-antibody binding, for use in pathogen detection and gene surveillance. However, there are an increasing number of reports that investigate the use of select biological substrates as "bio-templates" for the patterning of inorganic materials. In particular, the macromolecular structures of viruses have proven to be useful scaffolds for the self-assembly of two- and three-dimensional nano-scaled structures that can be spatially patterned using genetic and/or chemical methods [1], [2], [3], [4], [5] and [6].

Inorganic deposition onto these bio-templates has been accomplished using a variety of methodologies including chemical cross-linking, genetic engineering, and electroless plating, resulting in the deposition of numerous inorganic compounds including metal particles, silica, metal oxides, and metal sulfides [7], [8], [9] and [10]. Virus-assembled inorganic nanostructures have been fashioned into conductive nanowires, field effect transistors, memory device components, and battery electrodes [11], [12], [13] and [14]. From these studies it is clear that inherent biologically properties of viruses, including self-assembly, genetic programmability and spatial patterning provide a novel scaffold for the assembly of inorganic compounds.

Coating of materials onto the TMV surface has relied on electrostatic interactions in aqueous solvents [8], [12], [17] and [18]. In these instances, the solution pH was adjusted so the charge of the coating particle and that of the biological template were mutually attractive. Recently, two approaches have arisen to modify biological surfaces to increase their reactivity: genetic modifications of the coat protein to generate novel reactive amino acid and peptides [1], [2], [3], [4], [11], [12], [19] and [20], and chemical modifications attaching reactive groups directly to the bio-template [10], [21] and [22]. However, one downside to using a biologically derived template is the lack particle stability at high metal ion concentrations [23]. Template instabilities reduce coating efficiencies, resulting in partial or incomplete metal coatings.

Biologically derived nanotemplates hold the potential to produce novel nanostructures of unique size, shape, and function. However, the inherent instabilities in these templates that give flexibility also inhibits their use in a diverse array of coating strategies, thus limiting their application. As such, it would be advantageous to discover a system and method to provide for a TMV surface having increased stability to overcome the shortcomings of prior art biological templates.

SUMMARY OF THE INVENTION

The use of biological molecules as templates for the production of metal nanoparticles and wires is often limited by the stability of the bio-template and its affinity for nucleating metal deposition. The present invention uses microbes, such as microbes (e.g., viruses, mold, fungi, spores, yeast, algae, protozoans, plankton), and preferably, viruses, viral capsids or bacterial cages as a model biological template which includes an intermediary thicker layer of metal oxide to confer colloidal stability to the bio-templates prior to the metal coating. Surprisingly, the present invention provides for an aniline layer positioned between the metal oxide layer and the bio-template surface that provides for an increased thickness of silica that maintains the stability of the metallic coated bio-template particle.

In one aspect the present invention provides for a metallic nanoparticle, comprising a bio-template core, an aniline layer contacting the surface of the bio-template, a metallic oxide layer deposited on the aniline layer, and a metal layer deposited on the metal oxide layer, wherein the metallic oxide layer is from about 5 nm to about 50 nm thick, and wherein the metallic nanoparticle has increased stability relative to a bio-template metallic nanoparticle that does not include an aniline layer In another aspect the present invention provides for a metallic nanoparticle comprising a TMV core, an aniline layer contacting the surface of the TMV, a metallic oxide layer deposited on the aniline layer, and a metal layer deposited on the metal oxide layer, wherein the metallic oxide layer is from about 5 nm to 50 nm thick, and wherein the metal nanoparticle has increased stability relative to a TMV metallic nanoparticle that does not include an aniline layer.

TMV encodes a rod-shaped particle 300 nm in length and 18 nm in diameter with a 4 nm diameter hollow inner channel. Each TMV particle is comprised of ~2130 identical protein subunits (SEQ ID NO: 1) of molecular weight 17.5 kDa that self-assemble in a helix around a single strand of genomic virus RNA. TMV particles are also stable in a wide range of temperatures (up to 60° C.) and pH values (~pH 2-10), making the virus a durable biological template. Therefore, this virus can be to create tailor-made nanostructure materials that exhibit improved structural stability and higher capacity.

The metallic oxide layer may include at least one metal selected from the group consisting of Al, Ti, Fe, Cu, Zn, Y, Zr, Nb, Mo, In, Si, Sn, Sb, Ta, W, Pb, Bi and Ce and having a valence of from 2 to 6. The form of the metal oxide may, for example, be $Al_2O_3$, $SiO_2$, $TiO_2$, $Fe_2O_3$, $CuO$, $ZnO$, $Y_2O_3$, $ZrO_2$, $Nb_2O_5$, $MoO_3$, $In_2O_3$, $SnO_2$, $Sb_2O_5$, $Ta_2O_5$, $WO_3$, $PbO$, $ZnO$, $ZrO2$, $Ga_2O_3$ or $Bi_2O_3$. Preferably, the oxide is a silicon dioxide $SiO_2$.

Another aspect of the present invention provides for a Tobacco mosaic virus (TMV) bio-template comprising:
- a TMV capsid comprising multiple protein subunits, wherein the capsid has an outer surface;
- an aniline layer positioned on at least a portion of the outer surface;
- a silica layer positioned on the aniline layer; and
- a metallic layer deposited on the silica layer, wherein the silica layer has sufficient thickness to confer colloidal stability to the bio-template prior to the metal coating.

In yet another aspect, the present invention provides for a method for fabricating a metalized TMV nanoparticle, the method comprising:
- providing a TMV template comprising protein subunits of SEQ ID NO.: 1 or functional equivalent composed of protein subunits having at least 90% homology to SEQ ID NO.: 1;
- treating the surface of the TMV with aniline in an amount to neutralize protein charge of the TMV surface amino acid residues;
- coating the aniline coated TMV with a metal oxide to provide for a thickness layer of at least 5 nm to about 20 nm; and
- depositing a metallic material on the surface of the metal oxide layer, thereby providing for increased stability of the metalized TMV nanoparticle The metallic material includes but is not limited to gold, silver, palladium, platinum, nickel, aluminum, nickel, copper and other conductive metals.

A still further aspect of the present invention provides compositions comprising nanostructures of the present invention adhering to a substrate that can be any geometric shape including spherical, triangular, planar, rectangular, etc and retained in a composition, wherein the nanostructures are substantially monodisperse in length, width, or length and width because of the continuity of the TMV core. The substrate surface is not particularly limited but can be for example substantially flat. Substrates such as glass, metals, polymeric materials, and cellulose can be used. Microfabrication methods can be used to prepare substrates and build up layers and appropriate surfaces.

The metalized bio-template can be arranged on the substrates in random or patterned positioning, such as a nanoarray of the TMV templates of the present invention.

Other aspects and advantages of the invention will be more fully apparent from the ensuing disclosure and appended claims.

DETAILED DESCRIPTION OF THE INVENTION

Figure 1:
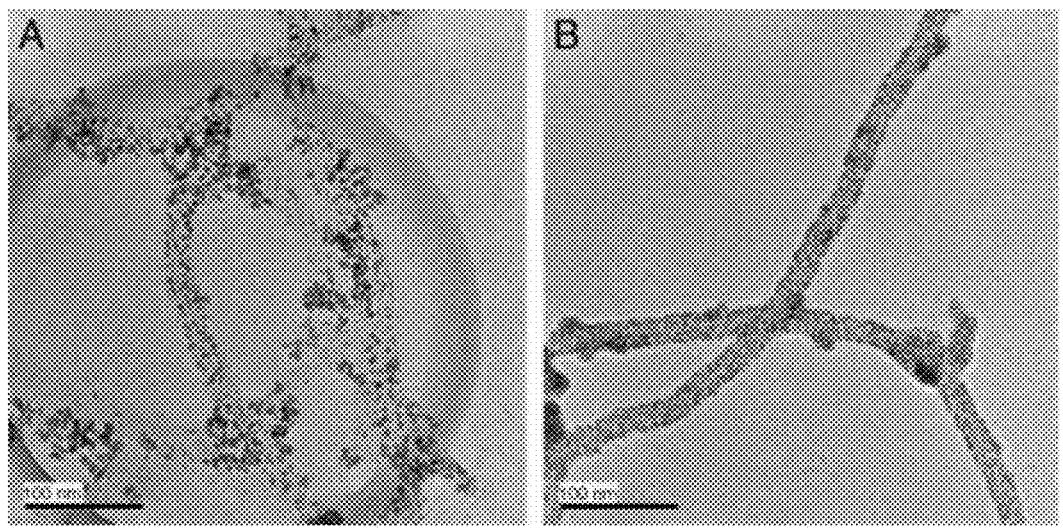
FIG. 1 shows the TEM images of (A) Pd-decorated thin-shell silica-coated TMV and (B) Pt-decorated thin-shell silica-coated TMV. Scale bar is equal to 100 nm.

As used herein, the terms "polypeptide," "protein" and "peptide" are used interchangeably to denote a sequence polymer of at least two amino acids covalently linked by an amide bond, regardless of length or post-translational modification (e.g., glycosylation, phosphorylation, lipidation, myristilation, ubiquitination, etc.). D- and L-amino acids, and mixtures of D- and L-amino acids are also included.

As used herein, the terms "homology" or "homologous," used in reference to polypeptides, refers to amino acid sequence similarity between two polypeptides. When an amino acid position in both of the polypeptides is occupied by identical amino acids, they are homologous at that position. Thus, by "substantially homologous" means an amino acid sequence that is largely, but not entirely, homologous, and which retains most or all of the activity as the sequence to which it is homologous and means that a sequence of the polypeptide is at least 70%, alternatively 85%, more likely 90%, and most likely 95% homology to a reference polypeptide. For polypeptides, the length of comparison to obtain the above-described percent homologies between sequences will generally be at least 25 amino acids or alternatively at least 50 amino acids, more likely at least 100 amino acids, and most likely 200 amino acids or more.

As set forth herein, substantially identical or homologous polypeptides include additions, truncations, internal deletions or insertions, conservative and non-conservative substitutions, or other modifications located at positions of the amino acid sequence which do not destroy the protein (as determined by functional assays, e.g., as described herein). A particular example of a substitution is where one or more amino acid is replaced by another, chemically or biologically similar residue. As used herein, the term "conservative substitution" refers to a substitution of one residue with a chemically or biologically similar residue. Examples of conservative substitutions include the replacement of a hydrophobic residue, such as isoleucine, valine, leucine, or methionine for another, the replacement of a polar residue for another, such as the substitution of arginine for lysine, glutamic for aspartic acids, or glutamine for asparagine, and the like. Those of skill in the art will recognize the numerous amino acids that can be modified or substituted with other chemically similar residues without substantially altering activity.

Virus arrays are a preferred embodiment and working examples are shown thereafter that demonstrate TMV arrays. However, the invention is not limited to this or any other plant virus. Animal and human virus may also be utilized, including respiratory track and flu viruses. Viruses can be used which are generally known for those of ordinary skill in the art. For example, a virus used herein can be a particle that can infect a cell of a biological organism. An individual virus, or a virus particle, also can be called a virion, can comprise one or more nucleic acid molecules, so called viral genome, surrounded by a protective protein coat known as a capsid. In some cases, viral nuclear acid molecules comprise both DNA and RNA. Viral DNA is usually double-stranded, either a circular or a linear arrangement, while viral RNA is usually single-stranded. However, examples of single stranded viral DNA and double-stranded viral RNA are also known. Viral RNA may be either segmented (with different genes on different RNA molecules) or nonsegmented (with all genes on a single piece of RNA). The size of the viral genome can vary significantly in size. Both DNA and RNA viruses can be used herein.

In viruses used herein, the viral capsid can comprise repeating units of one or a few different proteins coded by the viral genome. These units are called protomers or capsomers. The viral capsid can have a variety of shapes. For example, the viral capsid can be helical (spiral-shaped) or icosahedral. One example of a virus with a helical viral capsid is tomato mosaic virus, while examples of viruses isosahedral viral capsids include Tomato Bushy Stunt Virus and Simian Virus 40. Some more complex viruses can have a capsid that is neither purely helical, nor purely isosahedral. Some more complex viruses may possess extra structures such as protein tails or a complex outer wall.

For example, some bacteriophages, i.e. viruses that can infect bacterial cells, may have a capsid comprising isosahedral head bound to a helical tail, which may also have a hexagonal base plate with many protruding protein fibres.

Viruses can vary in size, as used herein. For example, a diameter of the viral capsid can be from about 10 nm to about 400 nm, usually about from about 10 nm to about 300 nm. Some viral capsids can have a significant length to diameter ratio. For example, capsids of some filoviruses can have a length up to 1400 nm and a diameter of only 80 nm.

Further, genetically engineered viruses and synthetically modified viruses can be used, such as genetically engineered Tobacco mosaic viruses TMV, wherein each of the genetically engineered Tobacco mosaic viruses comprises a multiplicity of subunits, wherein at least one of the subunits comprises at least one mutation, substitution, or addition in the amino acid residue of the virus but retaining substantial homology to the wild protein. Preferably, the genetically engineered TMV includes additional thiol containing amino acid residues.

In addition to viruses, other pathogens, including cellular parasites like malaria, are possible. Cell organelles (including but not limited to ribosomes, cellular nuclei, and other vesicles and cellular apparatuses) are also possible. TMV forms a rod-shaped particle 18 nm in diameter and 300 nm in length with a 4 nm diameter hollow inner channel.

TMV particles comprise ~2130 identical protein subunits of molecular weight 17.5 kDa that self-assemble in a helix around a single strand of genomic virus RNA [15]. Furthermore, TMV particles are stable in a wide range of temperatures (up to 60 C.) and pH values (pH ~2-10) [16], making TMV a viable template for a wide range of plating techniques.

The use of biological molecules as templates for the production of metal nanoparticles and wires is often limited by the stability of the bio-template and its affinity for nucleating metal deposition. Comparison results, shown herein, indicate that the unmodified TMV particle can function as a template for the growth of thin (<1 nm) silica layers. However, this thin silica shell did not enhance the stability of the template during metal deposition.

Silica-coated ($SiO_2$) TMV has been previously reported [7], [10] and [22]; however, the present invention is the first time a successful approach to produce thicker shell silica-modified TMV templates with enhanced stability has been shown. Also, investigated herein was the creation of a TMV core with alternating silica-metal-silica shells to produce multi-layer coatings that take advantage of traditional silica chemistry and stability. The hydrolysis and condensation of silica are widely studied phenomena; the condensation of tetraethylorthosilicate (TEOS) has been exploited to create nanotubes from surfactant-based assemblies [25] and [26] and polymer templates [27]. Chemical modifications, such as polymers or silica shells, provide functionality to biological molecules increasing their reactivity and stability [21], [22] and [28]. In the case of silica, the hydroxyl groups on hydrophilic silica surface provide reactive sites that permit interaction with inorganic ions [29], [30], [31] and [32]. Alternatively, the use of crosslinking molecules has been extensively investigated to facilitate coatings of gold and silver onto silica particle surfaces [32], [33], [34] and [35].

The present invention shows the development of a silica coating strategy that promotes not only the stability of the bio-template but also its affinity for metal ions. The silica provides a surface that is readily adaptable to mineralization strategies through the use of tin or crosslinking molecules. The oxide layer may be formed from a deposition technique, such as vapor deposition. The vapor deposition of $SiO_2$ is a well established technique for the controlled deposition of a variety of substrates. For example, an Edwards Vapor deposition module allows the deposition of a coating of $SiO_2$.

Figure 9:
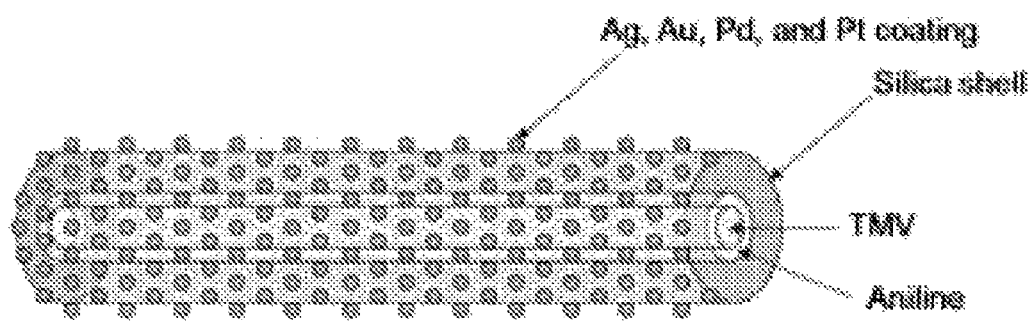
FIG. 9 shows polymerized aniline on TMV allows for thick silca shells to be grown on the surface of the virus. These templates are the foundation for tailorable metalized rod shaped particles.

Enhanced bio-template stability was achieved using an aniline polymerization step prior to silica coating. This aniline step serves to neutralize protein charge and hydrophobic features that likely interfered with silica shell formation. Once encased in silica, the TMV bio-templates provided a highly stable and robust platform for the deposition of metals at high densities as shown in FIG. 9. The present invention provides a surface suitable for long term storage, sonication, organic solvents, and in the case of surface-attached TMV resistant to drying effects. Besides producing a robust bio-template for the production of nanoparticles, this silica shell process allows the multi-layering of materials over the bio-template to create novel composites, potentially useful for conducting electrons and optical properties.

A thin coated silica TMV of the prior art was compared to that of the present invention to determine the increased stability of the metal nanoparticles of the present invention. In order to achieve this comparison, two silica-coated TMV templates were investigated; the first consists of a previously reported thin silica shell directly formed on the virus surface [22], and the second investigates the use of an aniline-precoat method [24] as a novel means to enhance the silica shell formation on the TMV surface.

Method and Materials

Pt and Pd Mineralization of Thin-Shell Silica-Coated TMV

As a comparison for showing the stability of the claimed invention a prior art thin-shell silica-coated TMV was prepared as described elsewhere [22]. The thinly silica-coated TMV particles were centrifuged and re-suspended in methanol to remove excess silica. Tin chloride ($SnCl_2$, Sigma-Aldrich 98%) in methanol was added to the solution to a final concentration of 1 mM and aged for 1 h. The sample was again centrifuged to remove excess $Sn^{2+}$, followed by the addition of hydrogen hexachloroplatinate hydrate ($H_2PtCl_6 \cdot H_2O$, Aldrich, 99.9+%) or sodium tetrachloropalladate ($Na_2PdCl_4$, Aldrich, 98%) in methanol to a final concentration of 0.2 mM and incubated for 1 h. An aqueous borane-dimethylamine complex (DMAB) (($CH_3$)$_2$NHBH$_3$, Aldrich, 97%) reducing agent was added post incubation to a final concentration of 0.4 mM. TEM and EDS samples were collected 15 min post DMAB addition. EDS samples were prepared by placing a drop of solution onto a TEM grid substrate and drying, prior to mounting on an SEM aluminum sample stub.

Preparation of Thick-Shell Silica-Coated TMV of the Present Invention

Solutions of TMV in water were prepared following standard purification techniques described elsewhere [20]. Aniline-coated TMV particles were prepared as described by Niu et al. [24], where 900 μL of water are mixed with 100 μL of 10 mg/mL TMV solution, 10 μL of aniline, and 10 mg of ammonium persulfate. Samples were allowed to react overnight followed by centrifugation and resuspension in 100 μL of water.

Aniline-coated TMV samples used for ethanol stability testing were mixed 1:10 with ethanol and allowed to incubate overnight. TEM samples were prepared on carbon-formvar grids and stained with UA. Silica-coating of aniline-coated TMV particles was carried out using the Stöber et al. method to produce silica spheres ~100~200 nm in diameter [36]. Tetraethylorthosilicate (Aldrich, 98%) and ammonium hydroxide ($NH_4OH$, Aldrich, 5N) were used as received. For coating the TMV template in silica, 18 μL of aniline-coated TMV was mixed in 437 μL ethanol, 25 μL of 5 M ammonia solution (30 wt %), and 19 μL TEOS on ice, with ammonia being added last. Particle solutions were centrifuged and resuspended in water with sonication after 2 h. Multilayer silica-shells were deposited by repeating this procedure with the metalized silica-coated TMV templates rather than aniline-TMV particles.

Ag, Au, Pd, and Pt Mineralization of Thick-Shell Silica-Coated TMV

Silver perchlorate hydrate ($AgClO_4 \cdot xH_2O$, Aldrich, 99%), hydrogen tetrachloroaurate trihydrate ($HAuCl_4 \cdot 3H_2O$, Sigma-Aldrich, 99.9+%), $Na_2PdCl_4$, potassium tetrachloroplatinate ($K_2PtCl_4 \cdot H_2O$, Aldrich, 99.9+%), DMAB, and 3-mercaptopropyl trimethylsilane (MPS) ($C_6H_{16}O_3SSi$, Aldrich, 95%) were used as received. Thick-shell silica-coated TMV particles were incubated overnight in a 1:10 ratio mercaptopropyl trimethylsilane (MPS) to ensure excess MPS in solution [33] and [37]. Functionalized silica templates (10 μL) were centrifuged and resuspended in 300 μL 0.1 M MOPS ($C_7H_{15}NO_4S$, Acros Organics, 99.5%) buffer, sonicated, and then placed on ice. To achieve platinum metallization, 0.05 M $K_2PtCl_4$ was added to the resuspended silica-TMV templates and incubated for 30 min, followed by reduction with 0.5 M DMAB. After 1 h, samples were centrifuged and resuspended in water. For silver, gold, and palladium a step wise procedure was used where metal salt addition followed by DMAB addition are broken up over 10 steps separated by 10 min incubations (for the case of Ag, this is performed in a darkroom) to the final concentrations of 0.05 M metal salt and 0.5 M DMAB. Particles were sonicated to break up aggregates. EDS samples were prepared by placing a drop of solution onto an aluminum SEM sample stub substrate and drying.

Growing Surface-Bound Thick-Shell Silica-Coated TMV

A gold-coated silicon chip was incubated overnight in the presence of 0.1 mg/mL TMV1cys in 0.1 M pH 7 phosphate buffer. The chip was then exposed to a solution consisting of 900 μL of water, 100 μL of 10 mg/mL wild-type TMV solution, 10 μL of aniline, and 10 mg of ammonium persulfate. Following aniline polymerization, treated gold surfaces were coated with silica by placing the chip into a solution of 18 μL of water, 437 μL ethanol, 25 μL of 5 M ammonia solution (30 wt %), and 19 μL TEOS on ice, with ammonia added last. Samples reacted for 1 h prior to being rinsed in ethanol and dried prior to imaging in the SEM. Both the TMV1cys mutant and wild-type TMV were prepared as previously described [20].

Characterization

TEM images of coatings on TMV templates were obtained using Zeiss EM 10CA TEM operated at 80 kV. All TEM samples were prepared without staining by using carbon/formvar coated copper grids. Platinum coated thick silica-shell TMV template samples were embedded in Spurr's resin sectioned to 70 nm thickness with a diamond knife. Sections were mounted on a carbon coated formvar copper grid. Energy dispersive X-ray spectroscopy (EDS), used to verify Ag, Au, Pd, Pt, and Si elemental presence, was conducted using an AMRAY 1820D SEM with an EDAX Genesis EDS system. EELS was obtained using an FEI Titan equipped with a Gatan Imaging Filter (GIF). High resolution TEM (HR-TEM) was conducted using a JOEL 2100FE TEM operated at 200 kV. Diffraction analysis was carried out using the public domain ImageJ image processing software [38].

Results and Discussion

Two methods for forming silica stabilized TMV nanoparticle templates were investigated, the first using a thin shell of silica on the TMV particle and the second exploring a thicker silica shell. Although metals (platinum and palladium) can be deposited on the thinly silica-coated TMV particles, the stability of the template in high metal ion solutions is relatively low, resulting in lower than desirable metallization of the particle and bending or breaking of the template structure to form curved, rather than straight, structures as seen in FIGS. 1A and B. This instability is most likely due to an incomplete coverage of silica on the TMV surface providing insufficient protection for the biological template under the harsh plating conditions needed to obtain the dense particle coatings. Attempts to enhance the silica coatings through additional silica growth failed as the template was unstable at the higher ammonia concentrations. It seems likely that the repulsive charge and hydrophobic features on the virion protein surface inhibits the complete coverage of nucleating silica, thus reducing coating continuity.

Figure 7:
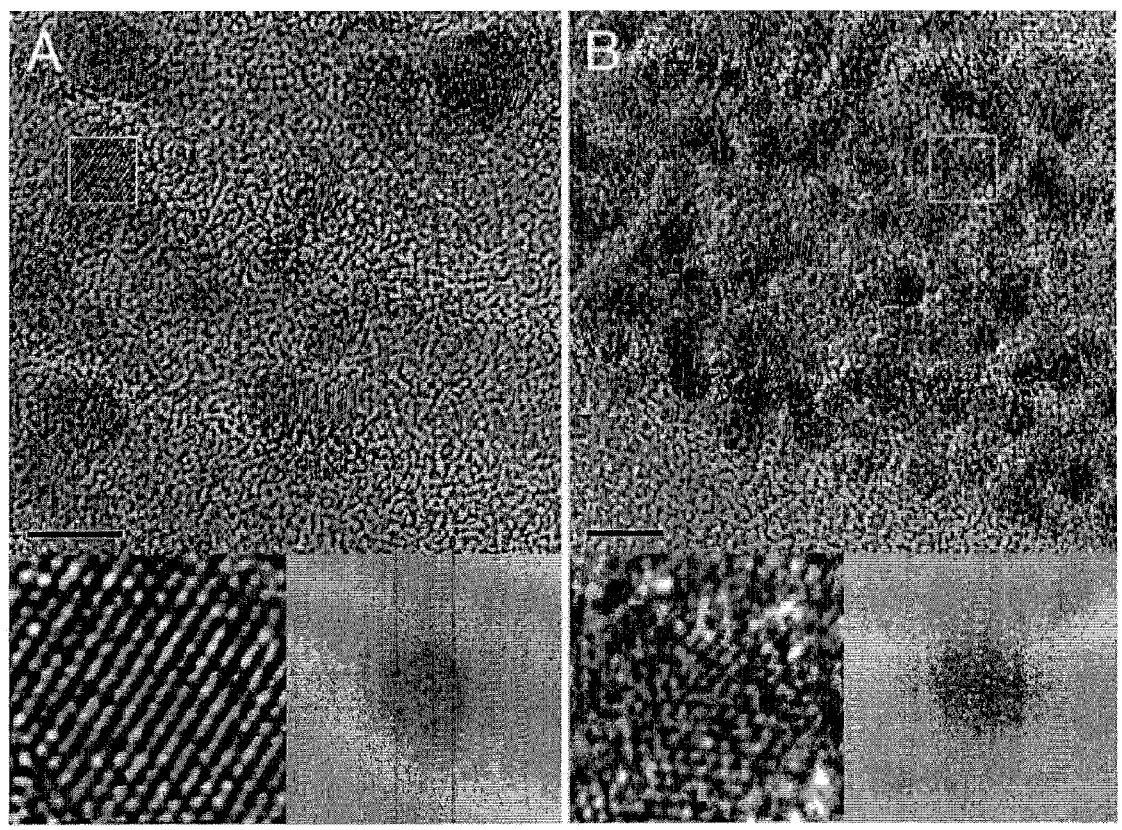
FIG. 7 shows HRTEM images of (a) Pd and (b) Pt on thin-shell silica-coated TMV templates and the corresponding crystal image and Fourier transforms identifying crystal structures. EDS spectra confirm the presence of Pd, Pt, Si, and Sn. Copper peaks represent signal from the support grid. Scale bar is equal to 5 nm.
Figure 7:
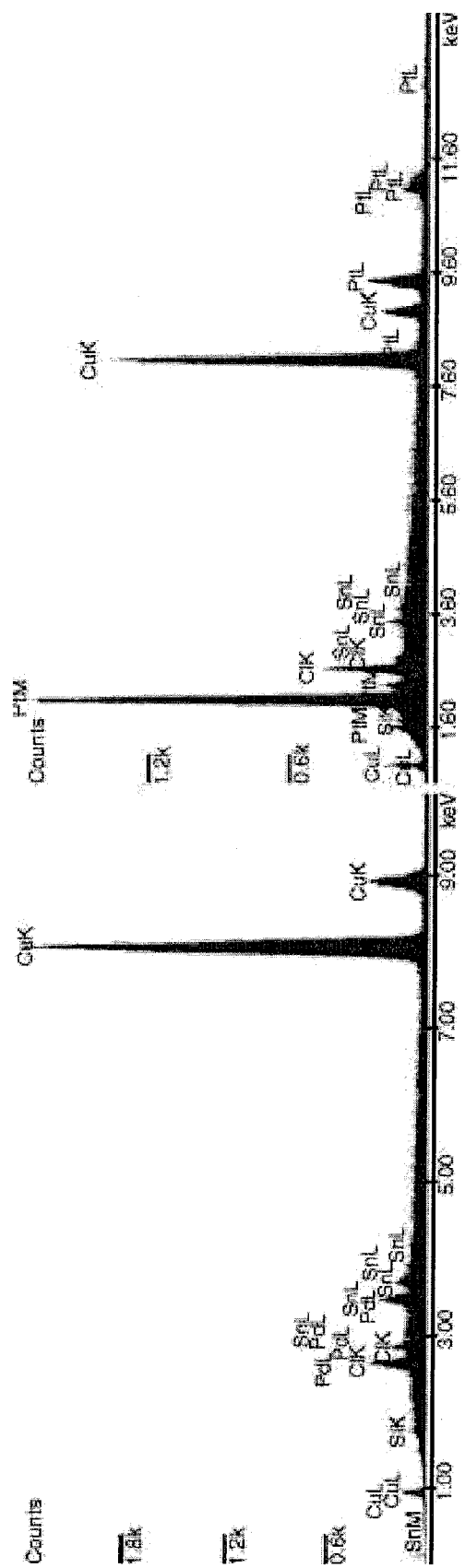

To achieve deposition of metal onto the thin silica-TMV template, a technique using the pretreatment of tin chloride is carried out to enhance the activity of the silica surface. In this case, $Sn^{2+}$ ions replace $H^+$ ions on the silica hydroxyl groups [39], where tin then behaves as a site-specific reducing agent on the silica surface [40], [41] and [42]. FIG. 1 shows examples of metal deposition on thin-shell silica-coated TMV particles. Thinly silica-coated TMV particles show palladium particle sizes of 6±3 nm and platinum particle diameters of 3±1 nm, with platinum deposition producing three times the number of particles as palladium. Platinum and palladium clusters were verified with EDS and HRTEM (see FIG. 7). The smaller platinum particle size is consistent with reported values for platinum deposition of <5 nm on a cysteine-modified TMV2cys template [12]. The varied size distribution in the palladium particles is also consistent with previously reported work on palladium-deposited TMV2cys templates [20]. Ultimately, the mineralized thin silica-shell TMV particles proved unsuited for the additional silica layer as they maintained their instability at the higher catalyst concentrations required for significant silica shell growth [36].

Figure 2:
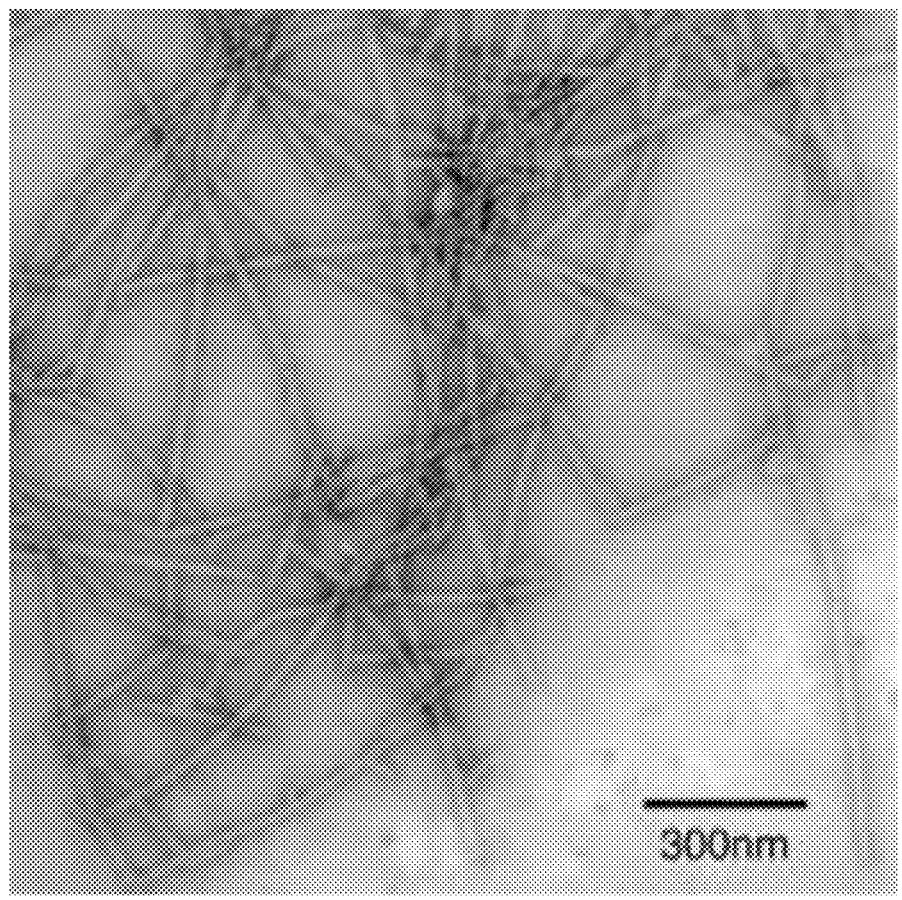
FIG. 2 shows the TEM image of UA stained aniline-TMV resuspended in EtOH.

In order to improve the stability of the templates in the biologically unfavorable plating conditions (high ionic strength or organic solvent-based solutions), and thus the quality of the metal coating, an alternative approach to obtain a thicker silica shell on the template was investigated. Aniline coatings on TMV have been shown to result in the alignment of TMV particles into micrometer-long threads and this was attributed to shielding of the charged groups on the TMV surface [24]. It was believed that masking of charges and hydrophobic surface features by aniline polymerization would produce a uniform and attractive surface for silica formation. Given that aniline has polymerized on the virion surface, the TMV particles were found to be stable in organic solvents, in addition to attracting silica monomers through their amine groups. Aniline-coated TMV incubated overnight in 90 wt % ethanol are shown in FIG. 2, demonstrating stability at higher alcohol concentrations than uncoated TMV [22]. These aniline-coated TMV are used as a template for creating elongated TMV-templated silica structures.

Figure 3:
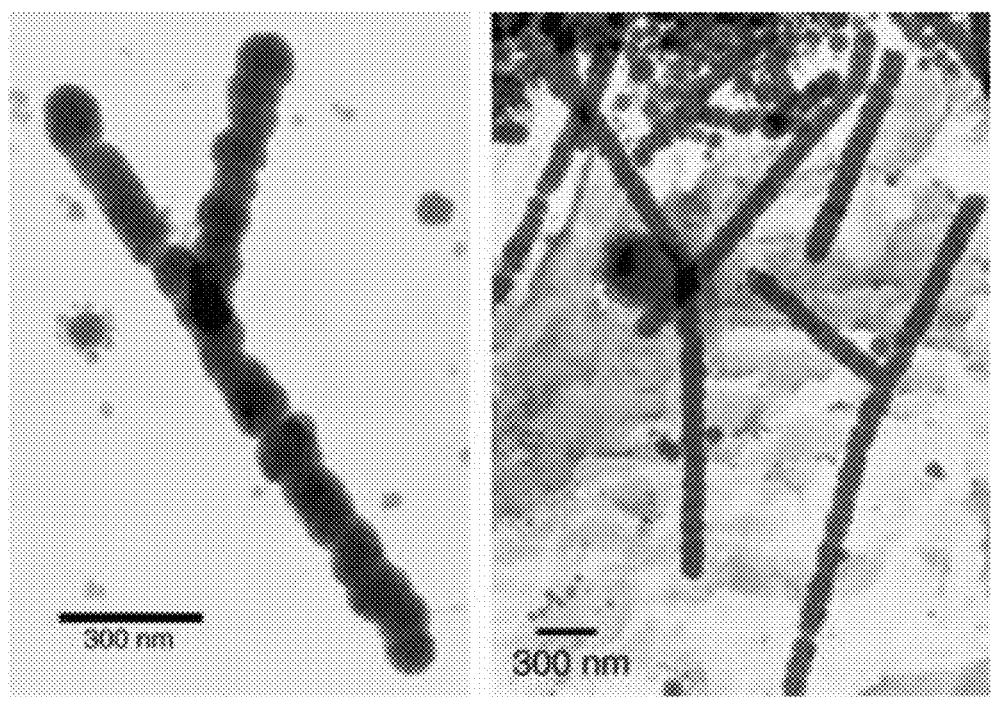
FIG. 3 shows TEM images of silica-coated aniline-TMV resuspended in water.

Growth of thick silica shells was accomplished via a sol-gel process. Taking advantage of the abundant amine groups in the aniline and their attraction to hydrolyzed silica (prior to ammonia addition) [43], in addition to the end-to-end alignment of TMV and the charge-neutralizing effects of polymeric coatings as described by Niu et al. [24], thickly coated TMV-templated silica rods were formed. Silica-coated TMV rods demonstrated dimensions of ~100 nm in thickness and lengths ranging from that of a single virion to several microns, as seen in FIG. 3. The undulating appearance of the silica coating on the TMV seems to be consistent with half the thickness of the silica-templated nanorod, possibly indicating the coatings are the result of multiple silica nanoparticles nucleating on the surface and growing together to form continuous silica shells. Temperatures were kept at 4 C. to enable the formation of silica on the TMV surface. At room temperature silica coatings fail to form, as the synthesis temperature affects the relative rates of particle formation and growth in the media, and particle formation and growth on the TMV surface.

Possible mechanisms for the fate of silica in this system are: (1) nucleation of silica in the media, (2) growth of silica in the media by aggregation of nuclei, (3) adsorption of soluble charged silicate species on the aniline groups on the surface of the TMV, (4) nucleation of silica on TMV surface, (5) growth of silica on TMV surface, and (6) deposition of silica nuclei on TMV. Lower temperatures tend to promote the sorption of charged silicate moieties (mechanism 3) and surface nucleation (mechanism 4) onto the aniline-functionalized TMV surfaces rather than the precipitation of silica particles in the media. In this case, mechanisms 1, 2, and 6 are slowed by the decrease in temperature and allow for the coating to be achieved [44] and [45].

The resulting silica rods are compatible with previously developed techniques for attaching inorganic materials onto silica surfaces using a crosslinking molecule [32], [33], [34] and [35]. In this case, mercaptopropyl trimethylsilane (MPS) was used as the crosslinking molecule, where the silane is capable of interacting with the silica surface on the TMV template and the sulfur group is free to interact with metal ions in solution.

Figure 4:
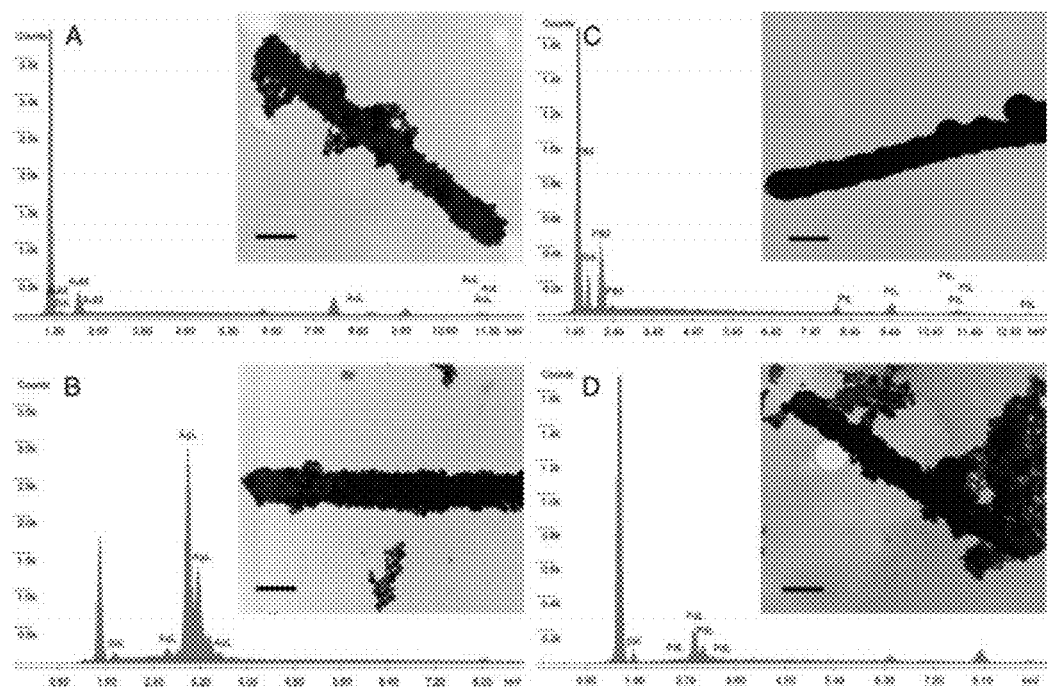
FIG. 4 shows TEM images and accompanying EDS spectra of (A) Au on thick-shell silica-coated TMV template, (B) Ag on thick-shell silica-coated TMV template, (C) Pt on thick-shell silica-coated TMV template, (D) Pd on thick-shell silica-coated TMV template. Al, Fe, and Cu peaks in the EDS spectra are due to background effects. Scale bar is equal to 100 nm.

Several examples of metalized MPS-functionalized silica-coated TMV, including silver, platinum, palladium, and gold, are shown in FIG. 4. Metal and silica presence verified with EDS is also shown in FIG. 4, where aluminum, iron, and copper peaks are confirmed as background effects resulting from the aluminum sample holder (data not shown). The coating of metals on the silica templates results in the formation of stable rods structures. In the case of platinum, it is clear a continuous metal coating was achieved. Using stepwise reductions of gold, silver, and palladium, continuous metal coatings were also achieved, as seen in FIG. 4. This process provides a means of combining self-assembly properties of the TMV with the enhanced stability and coatings of silica to produce a unique template for the production of nanowires.

Figure 5:
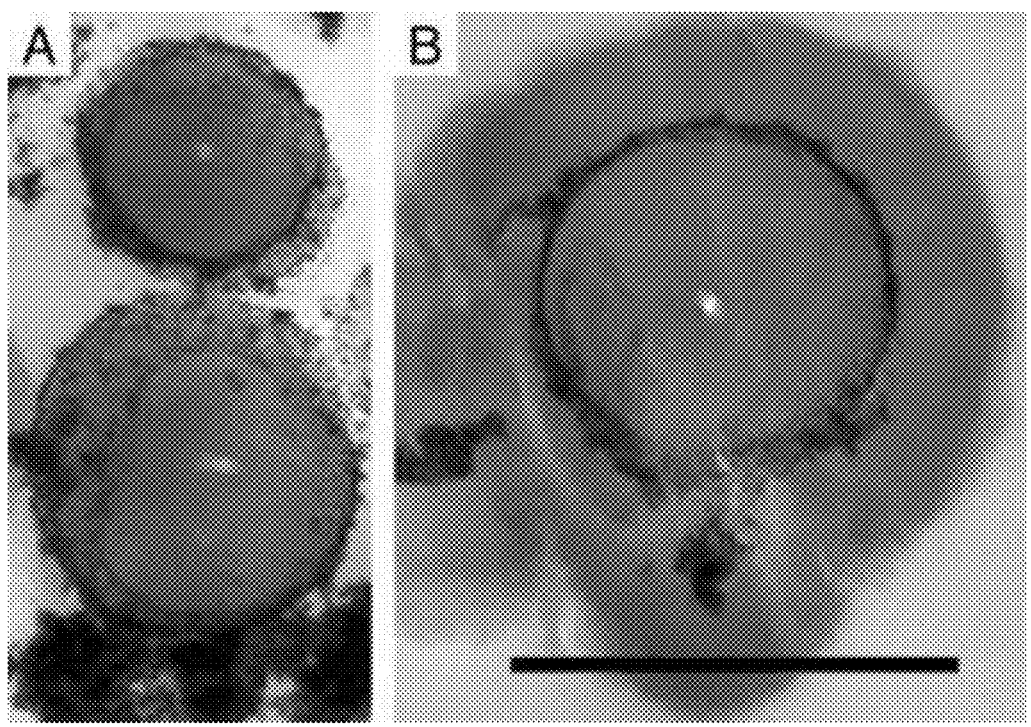
FIG. 5 shows TEM images showing cross-sections of (A) Pt on thick silica-coated TMV and (B) an additional thick-shell silica layer on the Pt-silica TMV. The hole in the center is the hollow inner channel of the TMV particle. Scale bar is equal to 100 nm.
Figure 8D:
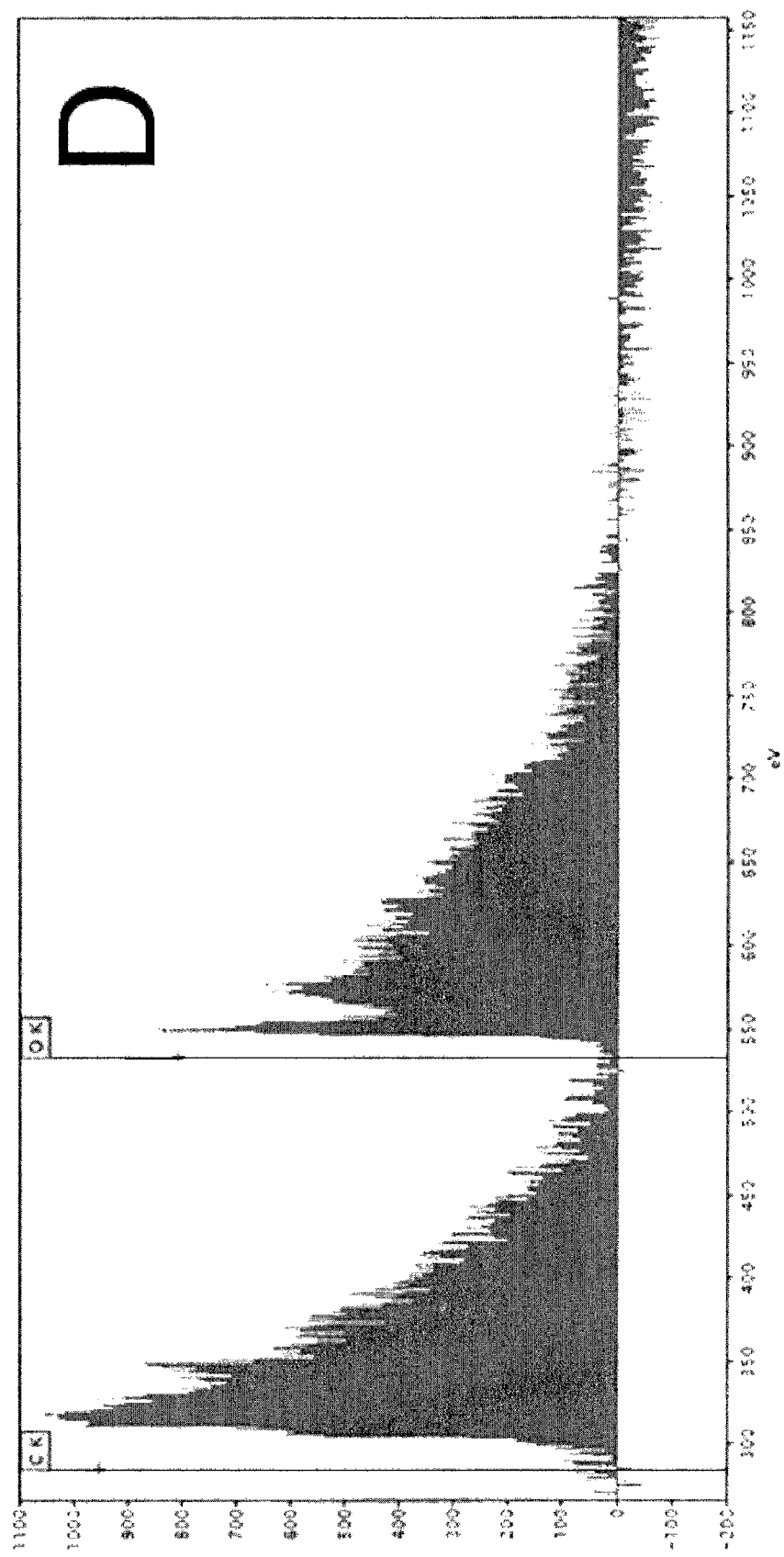
FIG. 8 shows EELS analysis of TMV-templated cross-sectioned nanoparticles. (a) Zero loss TEM image of a cross-sectioned resin-embedded SiPtSi TMV. (b) Higher magnification of the TMV hole at the center of the cross-section. (c) Corresponding EELS carbon map showing carbon presence in white. (d & e) EELS spectra showing presence of C, O, Si and Pt and (f) the corresponding TEM image of cross-sectioned PtSi layered TMV.
Figure 8E:
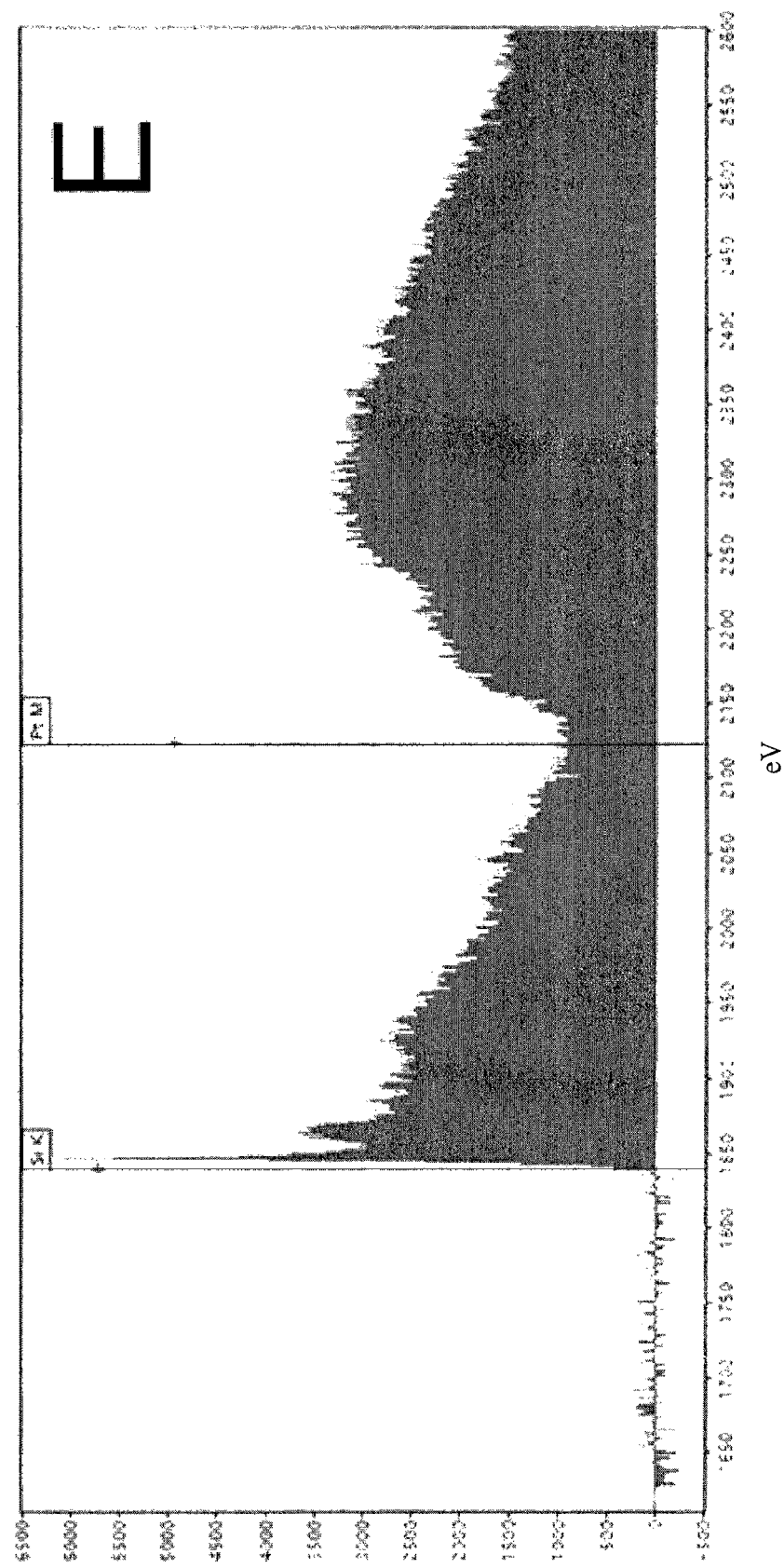

To create the multilayered particles, previously described techniques were used with silica particles [32], [33], [34] and [35]. These coatings are useful for shielding the metal surfaces from oxidation and enhancing colloidal stability [34]. Cross-sections of multilayered platinum-silica TMV-templated particles are shown in FIG. 5. Specifically, the metalized silica-TMV uncoated is shown in FIG. 5a, and then coated by a secondary layer of silica (FIG. 5b). The hole in the center of the image likely represents the TMV inner-channel. EELS confirms the expected presence of carbon around the hole and the presence of silica and platinum on the sample (see FIG. 8). The areas where platinum particles appear to be heading toward the inside of the cross-sectioned silica are likely caused by the varying silica coating thickness on the TMV surface (FIG. 3) and imperfect alignment of the sample in the resin. These multilayered TMV particles show regions of conducting material (metals) separated by silica layers which can potentially serve as an insulating material between multiple metal coatings or from the environment. These types of assemblies open the possibility for creating novel composites with potentially new conducting and or optical properties.

Figure 6:
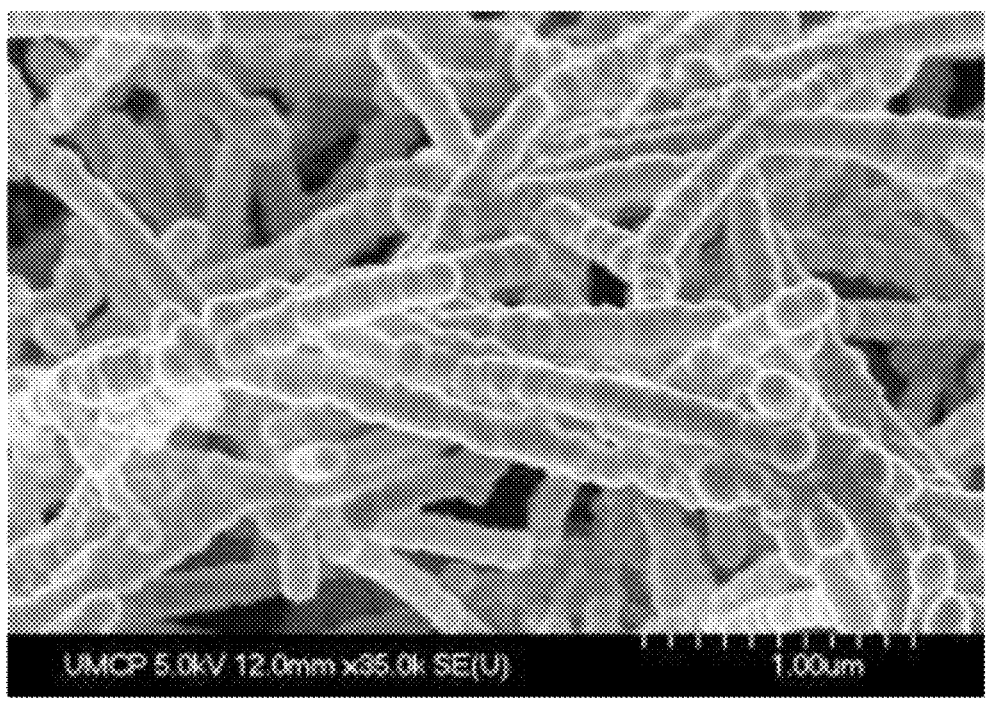
FIG. 6 shows SEM image showing thick-shell silica-coated aniline-TMV grown on an Au surface.

The attachment of the silica-coated TMV to surfaces was also investigated. In this case, a cysteine-modified TMV1cys [46] was attached to a gold surface as the template, prior to polymerization with aniline. Silica-coating after surface attachment results in TMV-templated silica surfaces, as seen in FIG. 6. In this case, the silica-coated TMV are attached at one end of the rod (3' end) through an exposed cysteine residue, producing high aspect ratio surfaces of oriented viruses. This method holds the potential to produce surface assembled virus templates of greater stability and length than previous examples [46].

REFERENCES

The references cited herein are hereby incorporated by reference herein for all purposes.

[1] C. B. Mao, C. E. Flynn, A. Hayhurst, R. Sweeney, J. F. Qi, G. Georgiou, B. Iverson and A. M. Belcher, *Proc. Natl. Acad. Sci. USA* 100 (2003), p. 6946.

[2] C. B. Mao, D. J. Solis, B. D. Reiss, S. T. Kottmann, R. Y. Sweeney, A. Hayhurst, G. Georgiou, B. Iverson and A. M. Belcher, *Science* 303 (2004), p. 213.

[3] S. W. Lee, C. B. Mao, C. E. Flynn and A. M. Belcher, *Science* 296 (2002), p. 892.

[4] C. E. Flynn, S. W. Lee, B. R. Peelle and A. M. Belcher, *Acta Mater.* 51 (2003), p. 5867.

[5] J. M. Hooker, E. W. Kovacs and M. B. Francis, *J. Am. Chem. Soc.* 126 (2004), p. 3718.

[6] C. Radloff, R. A. Vaia, J. Brunton, G. T. Bouwer and V. K. Ward, *Nano Lett.* 5 (2005), p. 1187.

[7] C. E. Fowler, W. Shenton, G. Stubbs and S. Mann, *Adv. Mater.* 13 (2001), p. 1266.

[8] E. Dujardin, C. Peet, G. Stubbs, J. N. Culver and S. Mann, *Nano Lett.* 3 (2003), p. 413.
[9] V. V. Hardikar and E. Matijevic, *J. Colloid Interface Sci.* 221 (2000), p. 133.
[10] W. Shenton, T. Douglas, M. Young, G. Stubbs and S. Mann, *Adv. Mater.* 11 (1999), p. 253.
[11] K. T. Nam, D. W. Kim, P. J. Yoo, C. Y. Chiang, N. Meethong, P. T. Hammond, Y. M. Chiang and A. M. Belcher, *Science* 312 (2006), p. 885.
[12] S. Y. Lee, J. W. Choi, E. Royston, D. B. Janes, J. N. Culver and M. T. Harris, *J. Nanosci. Nanotechnol.* 6 (2006), p. 974.
[13] R. J. Tseng, C. L. Tsai, L. P. Ma and J. Y. Ouyang, *Nat. Nanotechnol.* 1 (2006), p. 72.
[14] K. Keren, R. S. Berman, E. Buchstab, U. Sivan and E. Braun, *Science* 302 (2003), p. 1380.
[15] K. Namba, R. Pattanayek and G. Stubbs, *J. Mol. Biol.* 208 (1989), p. 307.
[16] G. Stubbs, *Semin. Virol.* 1 (1990), p. 405.
[17] W. L. Liu, K. Alim, A. A. Balandin, D. M. Mathews and J. A. Dodds, *Appl. Phys. Lett.* 86 (2005).
[18] M. Knez, M. Sumser, A. M. Bittner, C. Wege, H. Jeske, T. P. Martin and K. Kern, *Adv. Funct. Mater.* 14 (2004), p. 116.
[19] H. M. Yi, S. Nisar, S. Y. Lee, M. A. Powers, W. E. Bentley, G. F. Payne, R. Ghodssi, G. W. Rubloff, M. T. Harris and J. N. Culver, *Nano Lett.* 5 (2005), p. 1931.
[20] S. Y. Lee, E. Royston, J. N. Culver and M. T. Harris, *Nanotechnology* 16 (2005), p. 5435.
[21] T. L. Schlick, Z. B. Ding, E. W. Kovacs and M. B. Francis, *J. Am. Chem. Soc.* 127 (2005), p. 3718.
[22] E. Royston, S. Y. Lee, J. N. Culver and M. T. Harris, *J. Colloid Interface Sci.* 298 (2006), p. 706.
[23] S. Y. Lee, J. N. Culver and M. T. Harris, *J. Colloid Interface Sci.* 297 (2006), p. 554.
[24] Z. Niu, J. Liu, L. A. Lee, M. A. Bruckman, D. Zhao, G. Koley and Q. Wang, *Nano Lett.* 7 (2007), p. 3729.
[25] M. Adachi, T. Harada and M. Harada, *Langmuir* 15 (1999), p. 7097.
[26] M. Adachi, T. Harada and M. Harada, *Langmuir* 16 (2000), p. 2376.
[27] I. Ichinose and T. Kunitake, *Adv. Mater.* 14 (2002), p. 344.
[28] M. Endo, H. X. Wang, M. Fujitsuka and T. Majima, *Chem. Eur. J.* 12 (2006), p. 3735.
[29] Y. Kobayashi, V. Salgueirino-Maceira and L. M. Liz-Marzan, *Chem. Mater.* 13 (2001), p. 1630.
[30] Y. T. Lim, O. O. Park and H. T. Jung, *J. Colloid Interface Sci.* 263 (2003), p. 449.
[31] S. Ahrland, I. Grenthe and B. Noren, *Acta Chem. Scand.* 14 (1960), p. 1059.
[32] M. Schierhorn and L. M. Liz-Marzan, *Nano Lett.* 2 (2002), p. 13.
[33] T. Pham, J. B. Jackson, N. J. Halas and T. R. Lee, *Langmuir* 18 (2002), p. 4915.
[34] Y. L. Shi and T. Asefa, *Langmuir* 23 (2007), p. 9455.
[35] J. H. Kim, J. S. Kim, H. Choi, S. M. Lee, B. H. Jun, K. N. Yu, E. Kuk, Y. K. Kim, D. H. Jeong, M. H. Cho and Y. S. Lee, *Anal. Chem.* 78 (2006), p. 6967.
[36] W. Stober, A. Fink and E. Bohn, *J. Colloid Interface Sci.* 26 (1968), p. 62.
[37] S. L. Westcott, S. J. Oldenburg, T. R. Lee and N. J. Halas, *Langmuir* 14 (1998), p. 5396.
[38] W. Rasband, ImageJ, 1.33u, National Institutes of Health, USA, 2004.
[39] I. P. Suzdalev, V. I. Goldanskii, E. F. Makarov, A. S. Planchinda and L. A. Korytko, *Sov. Phys. JETP* 22 (1966), p. 979.
[40] Y. Kobayashi, V. Salgueirino-Maceira and L. M. Liz-Marzan, *Chem. Mater.* 13 (2001), p. 1630.
[41] Y. T. Lim, O. O. Park and H. T. Jung, *J. Colloid Interface Sci.* 263 (2003), p. 449.
[42] Y. Kobayashi, Y. Tadaki, D. Nagao and M. Konno, *J. Colloid Interface Sci.* 283 (2005), p. 601.
[43] D. Christendat, T. Abraham, Z. Xu and J. Masliyah, *J. Adhes. Sci. Technol.* 19 (2005), p. 149.
[44] R. K. Iler, The Chemistry of Silica: Solubility, Polymerization, Colloid and Surface Properties, and Biochemistry, John Wiley & Sons, New York (1979).
[45] C. J. Brinker and G. W. Scherer, Sol-Gel Science: The Physics and Chemistry of Sol-Gel Processing, Academic Press, Boston (1990).
[46] E. Royston, A. Ghosh, P. Kofinas, M. T. Harris and J. N. Culver, *Langmuir* 24 (2008), p. 906.

That which is claimed is:

1. A Tobacco mosaic virus (TMV) bio-template comprising:
 a TMV capsid comprising multiple protein subunits, wherein the capsid has an outer surface;
 an aniline layer positioned on at least a portion of the outer surface;
 a metal oxide layer positioned on the aniline layer, wherein the metal oxide layer is $SiO_2$; and
 a metallic layer deposited on the metal oxide layer, wherein the metal oxide layer has sufficient thickness to confer colloidal stability to the bio-template prior to the metal coating.

2. The bio-template according to claim 1, wherein the metallic layer is a conductive metal.

3. The bio-template according to claim 1, wherein the metallic layer is gold, silver, palladium, platinum, aluminum, nickel, or copper.

4. The bio-template according to claim 1, wherein the metal oxide layer is from about 5 nm to about 20 nm in thickness.

5. The bio-template according to claim 4, exhibiting increased stability relative to a TMV bio-template that does not include an aniline layer.

6. The bio-template according to claim 1, wherein the protein subunit comprises the amino acid sequence of SEQ ID NO. 1 or an amino acid sequence having at least 95% homology thereof.

7. The bio-template according to claim 1, further comprising a surface for attachment of a cysteine modified TMV capsid to the surface as the template prior to polymerization with aniline of the TMV bio-template.

8. A method for fabricating a metalized TMV nanoparticle, the method comprising:
 providing a TMV template comprising multiple protein subunits;
 treating the TMV template with aniline in an amount to neutralize protein charge of the TMV surface amino acid residues;
 coating the aniline coated TMV with a metal oxide to provide for a layer of the metal oxide having a thickness of at least 5 nm to about 20 nm, wherein the metal oxide layer is $SiO_2$; and
 depositing a metallic material on the metal oxide surface, thereby providing for increased stability of the metalized TMV nanoparticle.

9. The method according to claim 8, wherein the metallic material is gold, silver, palladium, platinum, aluminum, nickel, or copper.

10. The method according to claim 8, wherein the metal oxide layer is from about 5 nm to about 20 nm in thickness.

11. The method according to claim 8, wherein the protein subunit comprises the amino acid sequence of SEQ ID NO. 1 or an amino acid sequence having at least 95% homology thereof.

12. The method according to claim 8, further comprising attaching the TMV template to a surface substrate before treating the TMV template with aniline.

13. A composition comprising TMV bio-templates according to claim 1, wherein the TMV-bio-templates are substantially monodispersed in length, width, or a combination thereof.

14. The composition according to claim 13, wherein the metallic layer is gold, silver, palladium, platinum, aluminum, nickel, or copper.

15. The composition according to claim 13, wherein the metal oxide layer is from about 5 nm to about 20 nm in thickness.

16. The composition according to claim 13, wherein the protein subunit comprises the amino acid sequence of SEQ ID NO. 1 or an amino acid sequence having at least 95% homology thereof.

* * * * *

SEQUENCE LISTING

```
<160> NUMBER OF SEQ ID NOS: 1

<210> SEQ ID NO 1
<211> LENGTH: 159
<212> TYPE: PRT
<213> ORGANISM: Tobacco mosaic virus

<400> SEQUENCE: 1

Met Ser Tyr Ser Ile Ser Thr Pro Phe Gln Phe Val Phe Leu Ser Ser
1               5                   10                  15

Ala Trp Ala Asp Pro Ile Glu Leu Ile Asn Leu Cys Thr Asn Ala Leu
            20                  25                  30

Gly Asn Gln Phe Gln Pro Gln Gln Ala Arg Thr Val Val Gln Arg Gln
        35                  40                  45

Phe Ser Glu Val Trp Lys Pro Ser Pro Gln Val Thr Val Arg Phe Pro
    50                  55                  60

Asp Ser Asp Phe Lys Val Tyr Arg Tyr Asn Ala Val Leu Asp Pro Leu
65                  70                  75                  80
```

-continued

```
Val Thr Ala Leu Leu Gly Ala Phe Asp Thr Arg Asn Arg Ile Ile Glu
            85                  90                  95
Val Glu Asn Gln Ala Asn Pro Thr Thr Ala Glu Thr Leu Asp Ala Thr
                100             105                 110
Arg Arg Val Asp Asp Ala Thr Val Ala Ile Arg Ser Ala Ile Asn Asn
        115                 120                 125
Leu Ile Val Glu Leu Ile Arg Gly Thr Gly Ser Tyr Asn Arg Ser Ser
        130                 135             140
Phe Glu Ser Ser Ser Gly Leu Val Trp Thr Ser Gly Pro Ala Thr
145                 150                 155
```